(12) United States Patent
Takesako et al.

(10) Patent No.: US 6,294,581 B1
(45) Date of Patent: Sep. 25, 2001

(54) INHIBITION OF IGA PRODUCTION

(75) Inventors: Kazutoh Takesako, Otsu; Hideharu Saito, Kusatsu; Ikunoshin Kato, Uji, all of (JP)

(73) Assignee: Takara Shuzo Co., Ltd., Kyoto (JP)

(*) Notice: Subject to any disclaimer, the term of this patent is extended or adjusted under 35 U.S.C. 154(b) by 0 days.

(21) Appl. No.: 09/646,350
(22) PCT Filed: May 11, 1999
(86) PCT No.: PCT/JP99/02414
§ 371 Date: Sep. 18, 2000
§ 102(e) Date: Sep. 18, 2000
(87) PCT Pub. No.: WO99/59567
PCT Pub. Date: Nov. 25, 1999

(30) Foreign Application Priority Data

May 15, 1998 (JP) .................................... 10-150754

(51) Int. Cl.$^7$ .............................. A61K 31/16; A61K 31/27
(52) U.S. Cl. .......................... 514/616; 514/478; 514/482
(58) Field of Search .................................... 514/478, 482, 514/579, 616

(56) References Cited

FOREIGN PATENT DOCUMENTS 9228233 (Abstract) * 5/1993 (AU) .

OTHER PUBLICATIONS

"A case of recurrent IgA nephropathy following renal transplantation uder tacrolimus (FK506)", Takao et al, Acta Urologica Japonica, (1997): Abstract.*

* cited by examiner

*Primary Examiner*—Zohreh Fay
*Assistant Examiner*—Brian-Yong Kwon
(74) *Attorney, Agent, or Firm*—Browdy and Neimark

(57) ABSTRACT

The production of IgA is selectively inhibited by orally administering 15-deoxyspergualin or pharmacologically acceptable salts thereof, thus preventing and treating IgA-associated immunological diseases such as IgA nephropathy.

3 Claims, No Drawings

INHIBITION OF IGA PRODUCTION

TECHNICAL FIELD

The present invention relates to suppression of IgA production, more specifically, to selective suppression of IgA production for preventing and treating immunological disorders caused by over-production of IgA antibodies in a human and an animal.

BACKGROUND ART

Immunoglobulins, which include an antibody and a protein structurally and functionally related therewith, are classified into five classes (IgA, IgD, IgE, IgM and IgG) based on their functional properties. Among these, IgAs are divided into two subclasses, i.e., serum IgA and secretory IgA (IgA1 and IgA2). The L-chains of the IgA1 are covalently bound to H-chains. On the other hand, the L-chains of the IgA2 are bound each other through S-S bonds instead of being bound to H-chains. 90% of the serum IgA is IgA1, whereas 60% of the secretory IgA is IgA2.

Sites of IgA production are present in submucosal plasma cells in, for example, a tunica propria of a mucous membrane of a digestive tract, in a salivary gland, in a mammary gland and the like. In a tunica propria of a mucous membrane of a digestive tract in a human, the number of IgA-producing cells is much greater than that of IgG-producing cells in the ratio about 20:1, in contrast to the ratio 1:3 (IgA:IgG) in a lymph node or a spleen. The IgA in mucosal secretions is produced as a dimer having one J-chain component and accompanied by a secretory piece (SC), which is only a little in the serum IgA. The secretory piece is added to the dimeric IgA molecule while it comes out from submucosal plasma cells in an intestine or a respiratory tract to mucosal secretions.

The production of an antibody in an organism is induced by stimulation with a certain antigen. For example, oral administration of a strain of an enterobacterium, Bifidobacterium longum, has been reported to increase the total amount of IgA in feces.

A substance capable of non-specifically stimulating antibody producing cells to deal with an antigen more effectively is often called an adjuvant. For example, cholera toxin, which is a causal toxin of diarrhea produced by Vibrio cholerae, is known to act on a mucous membrane of a small intestine and alter the ionic permeability of the membrane. The alteration results in an excretion of a large amount of electrolytes and water from the small intestine to cause diarrheal conditions. Cholera toxin B subunit, which is a detoxified component prepared by removing the substantial portion of the toxin, is known to be able to elicit an immune response which promotes IgA antibody production (to be able to induce IgA) after penetration into a mucosal membrane of a small intestine, and thus serve as an adjuvant.

IgG, which is about 65% of serum immunoglobulins (Ig) in humans, consists of antibodies against almost all of the antigens and plays an important role in systemic protective immunity. On the other hand, IgA plays an important role in local immune reaction. The secretory IgA in mucosal secretions inhibits the binding of a highly pathogenic microorganism or an allergen to a mucous membrane. Therefore, IgA not only prevents an infection but also prevents a component in foods that may act as an allergen from passing through a digestive tract wall by binding to it.

For example, in case where an extracellular toxin is secreted from microbial cells, the biological defense by antibodies depends on the direct action of antibodies bound to the surface of the microorganism. Thus, antibodies can exert various effects by direct binding to a microorganism.

However, the IgA is also known to act pathologically on a living body. For example, IgA nephropathy is an immunological disorder that is caused by excess immune reactions of IgA in response to an antigen and by deposition of immune complexes mainly containing IgA onto a glomerulus of a kidney. It is believed that the onset of the nephropathy is caused by long-term high IgA antibody titers. The titer of IgA antibody in blood from a patient with IgA nephropathy is quite higher than that in a healthy and normal individual. However, it has not been demonstrated whether the IgA involved in the formation of the immune complex is of the serum type from sites other than a mucous membrane (spleen, bone marrow, peripheral blood, etc.) or of the secretory type from a mucous membrane (digestive tract, respiratory apparatus, etc.).

It is suspected that the causal agent of the immune reaction is an antigenic stimulus mainly in an upper airway and a digestive tract. Candidate antigens include foods (e.g., gluten, milk, soybean), bacteria (e.g., Haemophilus parainfluenzae), viruses (e.g., Cytomegalovirus, Adenovirus, Epstein-Barr (EB) virus) [Tomino, Y., Bio. Clinica, 12(6):375–379 (1997)]. For example, it has been demonstrated that a component of Haemophilus parainfluenzae (HP) and an IgA-type anti-HP antibody are present in the glomerulus and serum in a patient with IgA nephropathy [Suzuki, S., Nakatomi, Y., Sato, H. et al., Journal of Allergy Clinical Immunology, 96:1152–1160 (1995)].

Although hypotheses concerning the cause of the IgA nephropathy and the mechanism of its development have been proposed as described above, many of them are still unclear. There is currently no specific therapy for the IgA nephropathy. Thus, a dietetic therapy or a pharmacotherapy is used. The dietetic therapy uses a low salt diet or a low protein diet. The pharmacotherapy uses an antiplatelet for suppressing blood coagulation in the glomerulus, an angiotensin converting enzyme inhibitor or a calcium antagonist for suppressing a rise in blood pressure, or an adrenocorticoid [Sakai, H., Bio. Clinica, 16:372–374 (1997)].

Effects of several immunosuppressive agents are currently examined by parenteral administration. However, since many of them systemically suppress immunological mechanisms such as IgG production and cellular immunity in addition to the suppression of the over-production of IgA, there is the high risk of causing a severe side effect. Therefore, such immunosuppressive agents have not been widely used clinically yet.

Examples of the immunosuppressive agents include 15-deoxyspergualin (designated as DSG hereinbelow) of formula 1:

wherein Gu represents a guanidino group. DSG is clinically used as an immunosuppressive agent in an injectable form for renal transplantation.

Alternatively, an effect of suppressing antibody production by parenterally administered DSG has been reported in JP-A 8-40887, JP-A 5-238932, Okubo, M. et al., Nephron, 60:336–341 (1992), Makino, M. et al., Immunopharmacology, 14:107–114 (1987), Inoue, K. et al., Proceedings Japanese Society Nephrology 30th Annual Meeting, pp. 191 (1987). The suppression of the production of antibodies of IgE, IgG, IgM and the like has been confirmed therein. However, DSG has not been reported to selectively suppress IgA.

On the other hand, the use of DSG in an oral composition has been described in Japanese Patent 2610621 and JP-A 8-40887. However, selective suppression of a specified class of antibody has not been disclosed.

OBJECTS OF INVENTION

One object of the present invention is to provide a useful and novel means for preventing and treating immunological disorders caused by over-production of IgA antibodies in a human and an animal.

The other objects a nd advantages of the present invention will be apparent from the description below.

SUMMARY OF INVENTION

The present inventors have confirmed that orally administered DSG effectively suppresses the production of secretory IgA and serum IgA by using an animal experimental model which has been made to produce IgA in mucosal tissues due to stimulation by an antigen. Surprisingly, it has further proved that strong systemic immunosuppressive effects which are observed upon parenteral administration (e.g., intravenous administration) of DSG such as significant effects of suppressing IgG production at the same level as that of effects of suppressing IgA production, is not observed. In addition, the present inventors have demonstrated that the oral administration of DSG to an animal in which the IgA production is increased predominantly suppresses IgA among antibodies to be suppressed by DSG.

Thus, in the present invention, DSG or a pharmacologically acceptable salt thereof, which is used for a patient in need of selective suppression of IgA antibody production, is given by oral administration, which is safer for a living body than conventional methods.

One embodiment of the present invention is a composition for oral administration to a human or an animal for selectively suppressing IgA production containing DSG or a pharmacologically acceptable salt thereof as an active ingredient.

Another embodiment of the present invention is use of DSG or a pharmacologically acceptable salt thereof for the manufacture of a composition for oral administration to a human or an animal for selectively suppressing IgA production.

Yet another embodiment of the present invention is a method for selectively suppressing IgA production in a human or an animal, characterized in that the method comprises orally administering DSG or a pharmacologically acceptable salt thereof to a human or an animal in need of selective suppression of IgA production.

According to the present invention, immune responses, particularly IgA antibody production, in response to an orally ingested antigen are suppressed, resulting in little or weak systemic immunosuppression and selective suppression of IgA production. Therefore, the present invention is useful for preventing and treating IgA-associated immunological disorder such as IgA nephropathy.

As used herein, "selective suppression" of IgA production means that IgA antibody production is significantly suppressed, and IgG antibody production and/or delayed hypersensitivity are not significantly suppressed.

DETAILED DESCRIPTION OF THE INVENTION

The active ingredient contained in the composition for oral administration for selectively suppressing IgA production according to the present invention may be either DSG or a pharmacologically acceptable salt of the DSG. DSG forms a salt with an acid. The acid for the formation of the salt may be an inorganic acid or an organic acid as long as it is pharmacologically acceptable. Preferable inorganic acids include, for example, hydrochloric acid, sulfuric acid, nitric acid and phosphoric acid. Preferable organic acids include, for example, acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, asparagic acid and glutamic acid.

Furthermore, in the present invention, one of spergualin-related compounds of formula 2:

wherein Gu represents a guanidino group, $X_0$ represents $(CH_2)_{1-6}$, or a phenylene group or $CH_2C_6H_4$ which may have a substituent, $X_1$ represents $(CH_2)_{2-7}$ or $CH=CH$, A represents CONH or NHCO; when A is CONH, $X_2$ represents a residue in which an α-amino group and an a-carboxyl group are removed from an α-amino acid or a residue in which an ω-amino group and an α-carboxyl group are removed from an ω-amino acid and a functional group may be presented in the residue; the stereochemistry of a residue derived from an α- or ω-amino acid having an optically active carbon is not specifically limited to L-, D- or DL-form; typical and specific examples include a residue in which an α-amino group and an α-carboxyl group are removed from an α-amino acid such as glycine, α-hydroxyglycine, α-methoxyglycine and serine as well as a residue in which an ω-amino group and an α-carboxyl group are removed from an amino acid such as β-alanine, γ-aminobutyric acid, δ-aminovaleric acid and ε-aminocaproic acid; when A is NHCO, $X_2$ represents a single bond, $CH_2NH$, $CH_2O$, or a substituted or unsubstituted lower alkylene group; the lower alkylene group includes, for example, a methylene group, an ethylene group and a propylene group, and the substituent thereof includes halogen such as fluorine, chlorine and bromine, a lower alkoxy group such as a methoxy group and an ethoxy group, and a hydroxyl group; as used herein, the term "lower" used for a substituent means that the substituent has 1–6, preferably 1–3 carbons; $X_3$ represents $NH-(CH_2)_4-N(R_{O1})-(CH_2)_3-NH-R_{O2}$, wherein $R_{O1}$ represents hydrogen or a residue in which a hydroxyl group is removed from a carboxyl group in α-phenylglycine, and $R_{O2}$ represents hydrogen or a residue in which a hydroxyl group is removed from a carboxyl group in an amino acid or a peptide;
which exhibits a similar effect of suppressing IgA production with that of DSG or a pharmacologically acceptable salt thereof as described above may be used. As used herein, "15-deoxyspergualins (DSG)" and pharmacologically acceptable salts thereof include a compound selected from these spergualin-related compounds represented by formula 2 and a pharmacologically acceptable salt thereof.

The spergualin-related compound is a derivative of spergualin isolated from a producer strain of genus Bacillus, which is known to have an anti-tumor activity, an immunopotentiating activity or an immunosuppressive activity depending on the type of the derivative (JP-A 58-62152, JP-A 61-129119, JP-A 64-90164). In addition, a method for producing DSG of formula 1 is disclosed in publications such as JP-B 61-23183.

DSG or a pharmacologically acceptable salt thereof which is contained as an active ingredient in the composition for oral administration according to the present invention may be produced according to the known method as described above or a modification thereof.

The composition for oral administration according to the present invention is formulated according to a known method by using DSG or a pharmacologically acceptable salt thereof alone or mixing it with an excipient or a carrier. DSG may be an active stereoisomer or a racemic compound.

Any pharmacologically acceptable substance may be used as an excipient or a carrier. For example, water, an alcohol, an animal or vegetable oil such as soybean oil, peanut oil, sesame oil and mineral oil, or synthetic oil is used as a liquid carrier. A saccharide such as lactose, maltose and sucrose, an amino acid, a cellulose derivative such as hydroxycellulose, an organic salt such as magnesium stearate, dextran, dextran sulfate, chondroitin sulfate, heparin, gelatin and the like are used as a solid carrier. These solid carries or liquid carriers can be used to prepare a formulation for oral administration such as a tablet, a capsule, a powder, a granule, a solution, a dry syrup or a microsphere formulation. A formulation in a single dosage form is preferable.

Additionally, an acid or an alkali or a suitable amount of buffer may be added to the composition according to the present invention in order to adjust pH.

Furthermore, it is desirable to add a surfactant such as sodium laurate or glycocholic acid, or βcyclodextrin to the composition for oral administration according to the present invention in order to increase the oral absorbability of DSG or a pharmacologically acceptable salt thereof contained as an active ingredient. It is also desirable to prepare a microsphere formulation using biodegradable lactate polymer, lactate-glycolate copolymer or the like in order to promote the uptake from a mucous membrane of digestive tract and increase the absorbability.

Although the content of DSG or a pharmacologically acceptable salt thereof in the composition for oral administration according to the present invention varies depending on the formulation, the content is usually 0.1–100% by weight, preferably 1–98% by weight. Generally, a tablet, a capsule, a powder or a granule contains 5–100% by weight, preferably 25–98% by weight of the active ingredient.

In the method for selectively suppressing IgA production according to the present invention, an effective amount of DSG or a pharmacologically acceptable salt thereof to suppress IgA production is orally administered to a human or an animal in need of selective suppression of IgA production.

The dose is determined depending on the age, body weight, disease conditions, purpose of therapy or the like of a human or an animal as a subject such as a mammal including a pet such as a dog or a cat and a domestic animal. The therapeutic dose for oral administration is preferably 0.01–5 mg/kg/day or 3–300 mg per adult human (weighing 65 kg) per day. More preferably, the dose is determined such that IgG production is not significantly suppressed at the least. Thus, the composition for oral administration according to the present invention is characterized in that it significantly suppresses IgA production even with a dose that does not significantly suppress IgG production at the least.

Certain laboratory animals such as mice grown in a specialized environment have not been sensitized immunologically to produce IgA. The effect of selectively suppressing IgA production of the composition for oral administration according to the present invention can be confirmed by using an experimental model that is made to produce mucosal IgA and serum IgA by oral administration of an antigen for mucosal immunological sensitization. On the other hand, a human or a domestic animal has already been subjected to mucosal immunological sensitization due to orally ingested heterologous antigens, for example, in foods, and produces IgA. Therefore, the composition for oral administration according to the present invention exhibits an effect of selectively suppressing the production of mucosal IgA and serum IgA against an orally inoculated antigen in a human or a domestic animal as it does in the experimental model.

Diseases due to mucosal IgA and/or serum IgA are exemplified by IgA nephropathy, for example. The oral composition according to the present invention is useful for treating IgA nephropathy.

The following Examples illustrate the present invention in more detail, but are not to be construed to limit the scope thereof. DSG used in Examples is a compound of formula 1 as described above.

EXAMPLE 1

Effect of suppressing secretory IgA production in response to orally administered antigen by DSG An effect of suppressing secretory IgA production by orally administered DSG was confirmed by measuring titers of anti-cholera toxin IgA antibodies in feces from mice orally given cholera toxin.

First, a cholera toxin solution and a DSG solution were prepared. Cholera toxin (Sigma) was dissolved in 0.2 M $NaHCO_3$ at a concentration of 50 µg/ml to obtain the cholera toxin solution. DSG (Takara Shuzo, lyophilized original drug) was dissolved in saline at a concentration of 5 mg/ml or 1.25 mg/ml to obtain the DSG solution.

Next, 0.2 ml of the cholera toxin solution was orally administered twice (on day 0 and day 7) to three groups of C57BL/6 mice (seven weeks old, female, five mice per group). Hereinbelow in this Example, the number of days is the one counted from day 0 on which the cholera toxin was administered for the first time. 0.2 ml/dose of the DSG solution at 5 mg/ml, the DSG solution at 1.25 mg/ml or saline was orally administered five times (once per day from day 7 to day 11) to the three groups of mice. The doses of DSG orally administered to the respective groups were 50 mg/kg, 12.5 mg/kg and 0 mg/kg, respectively. Feces were collected from the mice of the respective groups on day 7 and day 14. Antibodies in 0.1 g of the feces were extracted with 1 ml of phosphate buffered saline (PBS). The extract is designated as a feces antibody extract hereinbelow. Feces on day 7 were collected before the administration of DSG.

The titer of IgA antibodies in the feces antibody extracts was measured by an ELISA method. 50 µl each of a cholera toxin solution at 10 µg/ml in 0.2 M $NaHCO_3$ was added to Immuno Modules (Nunc), which were allowed to stand at 4° C. for 16 hours to coat the cholera toxin to obtain a solid phase for the ELISA method. After the solid phase was then blocked with a BSA solution containing 1% (w/v) bovine serum albumin (Sigma) dissolved in PBS, 50 µl each of the feces antibody extracts was added thereto, then reacted at 37° C. for 1 hour. 50 µl of horseradish peroxidase (HRP)-labeled rabbit anti-murine IgA antibody (Zymed) was added and reacted at 37° C. for 1 hour. 50 µl of an ABTS solution containing 2.75 mg/ml of azino bis-ethylbenzothizoline sulfonic acid (ABTS, a substrate for HRP, nacalai tesque) dissolved in citrate-phosphate buffer was then added thereto, reacted at room temperature for 15 minutes, and the absorbance at wavelength of 405 nm ($OD_{405}$) was then measured.

The results are shown in Table 1. In Table 1, the increased amount of secretory IgA antibody production means the difference between the amount of the IgA production on day 7 and that on day 14. The difference is expressed by the difference between the $OD_{405}$ value with the feces antibody extract of day 7 and the $OD_{405}$ value with the feces antibody extract of day 14 (mean±standard deviation).

TABLE 1

| Dose of DSG (mg/kg) | Increased amount of secretory IgA antibody production | Significant difference p |
|---|---|---|
| 0 | 0.409 ± 0.091 | |
| 12.5 | 0.249 ± 0.092 | <0.05 |
| 50 | 0.082 ± 0.017 | <0.0001 |

As seen from the results in Table 1, the oral administration of DSG at 50 mg/kg and 12.5 mg/kg resulted in significant decrease in the increased amount of secretory IgA production in response to the orally administered antigen as compared with that observed for the group received no DSG. These results confirm the effect of suppressing IgA production by the orally administered DSG.

EXAMPLE 2

Effect of selectively suppressing IgA production in response to orally administered antigen by DSG The effect of suppressing antibody production by orally administered DSG was confirmed by measuring the titer of anti-cholera toxin IgA antibody in feces, as well as the titer of anti-cholera toxin IgA antibody and anti-cholera toxin IgG antibody in blood from a mouse orally received cholera toxin.

Cholera toxin was orally administered to five groups of C57BL/6 mice (seven weeks old, female, five mice per group) as described in Example 1. 0.2 ml/dose of one of three DSG solutions or saline was orally administered ten times (once a day, from day 7 to day 17 excluding day 13) to four groups of mice for cholera toxin administration. The solutions contained DSG at 5 mg/ml, 1.25 mg/ml or 0.313 mg/ml dissolved in saline. The doses of DSG orally administered to the respective groups were 50 mg/kg, 12.5 mg/kg, 3.13 mg/kg and 0 mg/kg, respectively. 0.2 ml/dose of a DSG solution at 0.313 mg/ml was intraperitoneally administered ten times (once a day, from day 7 to day 17 excluding day 13) to the remaining one group of mice for cholera toxin administration. The dose of intraperitoneally administered DSG was 3.13 mg/kg.

Feces were collected from mice from the respective groups on day 7 and day 18. Antibodies were extracted with 1 ml of PBS from 0.1 g of the feces. The extract is designated as a feces antibody extract hereinbelow. The feces of day 7 were collected before the administration of DSG.

On the other hand, blood was partially collected on day 7 from orbital venous plexus of a mouse from each group under etherization and the whole body blood was collected on day 18. Sera were separated from the thus-obtained blood and diluted 50-folds. The dilution is designated as a blood antibody sample hereinbelow. The blood on day 7 was collected before the administration of DSG.

The titer of IgA antibodies against cholera toxin in the feces antibody extract or the blood antibody sample was measured by an ELISA method. The measurement was carried out as described in Example 1. The blood antibody sample was also used to determine the amount of IgG antibodies against cholera toxin produced in blood. The solid phase used for the titration of antibodies by the ELISA method is the same as that used for the titration of IgA antibodies by the ELISA method in Example 1.

After the solid phase was blocked with a BSA solution as described in Example 1, 50 µl each of the antibody samples was added thereto, and then reacted at 37° C. for 1 hour. 50 µl of HRP-labeled rabbit anti-murine IgG antibody (Zymed) was added and reacted at 37° C. for 1 hour. 50 µl of a 2.75/ml ABTS solution was then added thereto, reacted at room temperature for 15 minutes, and the absorbance at wavelength of 405 nm ($OD_{405}$) was then measured.

The results are shown in Table 2. Table 2 shows a variety of the differences between the amount of antibodies produced on day 7 and that on day 18. The difference is expressed by the difference between the $OD_{405}$ value with the feces antibody extract or the blood antibody sample of day 7 and the $OD_{405}$ value with the feces antibody extract or the blood antibody sample of day 18 (mean±standard deviation)

TABLE 2

| DSG Dose | Antibody titer | | |
|---|---|---|---|
| (mg/kg) | Secretory IgA | Blood IgA | Blood IgG |
| 0 | 0.308 ± 0.075 | 0.051 ± 0.013 | 0.493 ± 0.148 |
| 3.13 (p.o.) | 0.327 ± 0.065 | 0.035 ± 0.012 | 0.472 ± 0.112 |
| 12.5 (p.o.) | 0.112 ± 0.116* | 0.028 ± 0.012* | 0.570 ± 0.107 |
| 50 (p.o.) | 0.009 ± 0.054** | 0.016 ± 0.020** | 0.330 ± 0.169 |
| 3.13 (i.p.) | 0.008 ± 0.016*** | −0.009 ± 0.009*** | 0.034 ± 0.035** |

In Table 2, the superscript symbols on the right of numbers, *,  and *, represent significant differences of $P<0.05$, $P<0.001$ and $P<0.0001$, respectively. Additionally, p.o. represents a group orally administered with DSG and i.p. represents a group intraperitoneally administered with DSG.

The effect of suppressing antibody production by intraperitoneally administered DSG in feces and blood is very strong. Production of either of the antibodies, secretory IgA, blood IgA or blood IgG, was completely suppressed, suggesting the generation of systemic immunosuppression. The oral administration suppressed the antibody production of secretory IgA and blood IgA in a dose-dependent manner. The low degree of suppression of antibody production by the oral administration as compared with that by the intraperitoneal administration as well as the absence of the suppression of the IgG production in blood suggest that the systemic immunosuppression by the administration was slight.

EXAMPLE 3

Suppression of antibody production and delayed hypersensitivity in response to subcutaneously administered antigen by DSG.

In contrast to Example 1 and 2, the effect of orally administered DSG on antibody production in response to a subcutaneously administered antigen was confirmed. Briefly, after ovalbumin was subcutaneously administered to a mouse, DSG was administered orally. The titer of anti-ovalbumin IgA antibody in murine feces, as well as the titer of anti-ovalbumin IgA antibody and the titer of anti-ovalbumin IgG antibody in blood were measured to confirm the effect. Additionally, the effect of DSG on delayed hypersensitivity against ovalbumin was confirmed. (1) Suppression of antibody production: An ovalbumin suspension for subcutaneous administration was prepared by mixing ovalbumin (Sigma) with Freund complete adjuvant at a concentration of 200 μg/ml. A DSG solution was prepared by dissolving DSG in saline at a concentration of 5 mg/ml, 1.25 mg/ml or 0.313 mg/ml as described in Example 1.

0.1 ml of the ovalbumin suspension was then subcutaneously administered twice (day 0 and day 14) to three groups of C57BL/6 mice (seven weeks old, female, five mice per group). Hereinbelow in this Example, the number of days is the one counted from day 0 on which the ovalbumin was administered for the first time. 0.2 ml/dose of the DSG solution or saline was then orally administered ten times (once a day, from day 14 to day 24 excluding day 20) to the three groups of mice for ovalbumin administration. The doses of DSG orally administered to the respective groups were 50 mg/kg, 12.5 mg/kg and 0 mg/kg, respectively. 0.2 ml/dose of a DSG solution at 0.313 mg/ml was intraperitoneally administered ten times (once a day, from day 14 to day 25 excluding day 20) to the remaining one group of mice for ovalbumin administration. The dose of intraperitoneally administered DSG was 3.13 mg/kg.

Feces were collected from mice from the respective groups on day 14 and day 25. Antibodies in 0.1 g of the feces were extracted with 1 ml of PBS. The extract is designated as a feces antibody extract hereinbelow. The feces of day 14 were collected before the administration of DSG.

On the other hand, blood was partially collected on day 14 from orbital venous plexus of a mouse from each group under etherization and the whole body blood was collected on day 25. Sera were separated from the thus-obtained blood and diluted 50- or 250-folds. The dilution is designated as a blood antibody sample hereinbelow. The blood of day 14 was collected before the administration of DSG.

The titer of antibodies against ovalbumin in the feces antibody extract or the blood antibody sample was measured by an ELISA method. The measurement was carried out as described in Example 2 for the ELISA method except that the antigen used for the solid phase was changed from cholera toxin to ovalbumin.

The subcutaneous administration of ovalbumin did not increase the amount of IgA antibody in the feces or the blood. On the other hand, the subcutaneous administration of ovalbumin increased the amount of IgG antibody in the blood. The results for the change in the amount of IgG antibody produced in blood are shown in Table 3. Table 3 shows the difference between the amount of a variety of antibodies produced on day 14 and that on day 25. The difference is expressed by the difference between the $OD_{405}$ value with the blood antibody sample of day 14 diluted 250-folds and the $OD_{405}$ value with the blood antibody sample of day 25 diluted 250-folds (mean±standard deviation).

TABLE 3

| Dose of DSG (mg/kg) | Blood IgG | Significant difference P |
|---|---|---|
| 0 | 0.437 ± 0.173 | |
| 12.5 (p.o.) | 0.286 ± 0.074 | |
| 50 (p.o.) | 0.125 ± 0.141 | <0.05 |
| 3.13 (i.p.) | 0.064 ± 0.080 | <0.001 |

In Table 3, p.o. represents a group orally administered with DSG and i.p. represents a group intraperitoneally administered with DSG.

The administration of DSG at 50 mg/kg significantly suppressed the IgG antibody production in blood, whereas the administration of DSG at 12.5 mg/kg did not significantly suppressed it. On the other hand, the intraperitoneal administration of DSG at 3.13 mg/kg suppressed the antibody production in blood more strongly than the oral administration of DSG at 50 mg/kg did.

The above-mentioned results show that the oral administration of DSG selectively suppresses the antibody production in response to an orally ingested antigen rather than that in response to a parenterally inoculated antigen.

(2) Suppression of delayed hypersensitivity: 25 μl of an aqueous solution of ovalbumin (400 μg/ml) was subcutaneously administered to a foot pad of a mouse in each of the experimental groups in Example 3(1) 24 days after the ovalbumin administration. Swelling in the foot pad was measured 24 hours after the subcutaneous administration of ovalbumin. The results are shown in Table

TABLE 4

| Dose of DSG (mg/kg) | Swelling in foot pad ($\times 10^{-2}$ mm) |
|---|---|
| 0 | 88.6 ± 57.2 |
| 12.5 (p.o.) | 83.2 ± 41.4 |
| 50 (p.o.) | 62.0 ± 24.8 |
| 3.13 (i.p.) | 22.8 ± 35.3 |

No difference was recognized between the swelling in foot pad observed for a group orally administered with DSG at 50 mg/kg and that observed for group without administration. On the other hand, the swelling in foot pad observed for a group intraperitoneally administered with DSG at 3.13 mg/kg was reduced as compared with that observed for a group without administration. Thus, it was suggested that oral administration of DSG does not suppress delayed hypersensitivity and does not cause the systemic immunosuppression due to DSG.

EXAMPLE 4

Preparation of oral composition for suppressing IgA antibody production

Granule 50 parts by weight of DSG, 600 parts by weight of lactose, 330 parts by weight of crystallized cellulose and 20 parts by weight of hydroxyprqpyl cellulose were mixed well, compacted using a roll-type compactor (Roller Compactor™), ground and put through a sieve between 16-mesh and 60-mesh to obtain granules.

Tablet 30 parts by weight of DSG, 120 parts by weight of crystallized lactose, 147 parts by weight of crystallized cellulose and 3 parts by weight of magnesium stearate were mixed using a V-type mixer and compressed to obtain tablets (300 mg/tablet).

As described above, the oral composition containing DSG or a pharmacologically acceptable salt thereof according to the present invention suppresses immune reaction in response to an orally ingested antigen, particularly IgA antibody production, whereas little or weak systemic immunosuppression is observed. Therefore, the oral composition containing DSG or a pharmacologically acceptable salt thereof according to the present invention can be used to treat and prevent IgA-associated immunological diseases such as IgA nephropathy.

What is claimed is:

1. A method for selectively suppressing IgA production in a human or an animal, characterized in that the method comprises orally administering 15-deoxyspergualin or a pharmacologically acceptable salt thereof to a human or an animal in need of selective suppression of IgA production.

2. The method according to claim 1, wherein said human or animal is one suffering from IgA nephropathy.

3. The method according to claim 1 wherein said 15-deoxyspergualin or pharmaceutically acceptable salt thereof is administered in an amount sufficient to suppress IgA production without significant suppression of IgC production and/or delayed hypersensitivity.

* * * * *